United States Patent
Baileykobayashi et al.

(10) Patent No.: US 10,829,523 B2
(45) Date of Patent: Nov. 10, 2020

(54) ANTI-TUMOR PEPTIDES AND USE THEREOF

(71) Applicants: TOAGOSEI CO., LTD., Tokyo (JP); NATIONAL UNIVERSITY CORPORATION NAGOYA, Aichi (JP); KEIO UNIVERSITY, Tokyo (JP)

(72) Inventors: Nahoko Baileykobayashi, Ibaraki (JP); Tetsuhiko Yoshida, Ibaraki (JP); Makoto Sawada, Aichi (JP); Jun Kudoh, Tokyo (JP); Tamami Adachi, Tokyo (JP); Yasuhiro Tonoyama, Tokyo (JP)

(73) Assignees: Keio University, Tokyo (JP); National University Corporation Nagoya, Aichi (JP); Toagosei Co., Ltd., Tokyo (JP)

( * ) Notice: Subject to any disclaimer, the term of this patent is extended or adjusted under 35 U.S.C. 154(b) by 0 days.

(21) Appl. No.: 15/815,453

(22) Filed: Nov. 16, 2017

(65) Prior Publication Data
US 2018/0141985 A1     May 24, 2018

(51) Int. Cl.
| | |
|---|---|
| *A61P 35/00* | (2006.01) |
| *C07K 14/46* | (2006.01) |
| *C07K 14/705* | (2006.01) |
| *C07K 14/47* | (2006.01) |
| *G01N 33/50* | (2006.01) |

(52) U.S. Cl.
CPC ............ *C07K 14/461* (2013.01); *C07K 14/47* (2013.01); *C07K 14/705* (2013.01); *G01N 33/5011* (2013.01); *C07K 2319/03* (2013.01); *C07K 2319/10* (2013.01); *C07K 2319/33* (2013.01)

(58) Field of Classification Search
None
See application file for complete search history.

(56) References Cited

FOREIGN PATENT DOCUMENTS

WO    WO-2013/186934 A1    12/2013

OTHER PUBLICATIONS

Hu, Jian et al, "Structural biology of transmembrane domains: efficient production annd characterization of transmembrane peptides by nmr." Prot. Sci. (2007) 16 p. 2153-2165.*
Dexter, Annette and Middleberg, Anton P. J.; "Peptides as functional surfactants", Ind. Eng. Chem. Res. (2008) 47 p. 6391-6398.*
Pang, Zhulin et al; "Selection of surfactants for cell lysis in chemical cytometry to study protein-dna interactions." Electrophoresis (2006) 27 p. 1489-1494.*
Song, Ho-Yeon et al, "In vitro cycotoxic effect of glyphosphate mixture containing surfactants." J. Korean Med. Sci. (2012) 27 p. 711-715.*
TMHMM transmembrane prediction program, run on http://www.cbs.dtu.dk/services/TMHMM/, on Apr. 22, 2019.*
Meng, E., et al., "The Impact of Hedgehog Signaling Pathway on DNA Repair Mechanisms lin Human Cancer", Cancers, 7, (2015), 1333-1348.

* cited by examiner

*Primary Examiner* — Fred H Reynolds
(74) *Attorney, Agent, or Firm* — Schwegman Lundberg & Woessner, P.A.

(57) ABSTRACT

The anti-tumor peptide provided by the present invention is a synthetic peptide having both amino acid sequences represented by the following (1) and (2):
  (1) an amino acid sequence constituting the transmembrane domain of transmembrane protein 141 (TMEM 141), or a modified amino acid sequence having deletion, replacement, or addition of one, two, or three amino acid residues of the amino acid sequence; and
  (2) an amino acid sequence functioning as a cell membrane penetrating peptide (CPP).

4 Claims, No Drawings

Specification includes a Sequence Listing.

ANTI-TUMOR PEPTIDES AND USE THEREOF

CROSS-REFERENCE TO RELATED APPLICATIONS

This application claims the benefit of Japanese Patent Application No. 2016-225236, filed Nov. 18, 2016, which is hereby incorporated by reference herein in its entirety.

TECHNICAL FIELD

The present invention relates to an artificially synthesized anti-tumor peptide which can inhibit proliferation of tumor cells (cancer cells), and a use thereof. Specifically, the present invention relates to a use of an artificial peptide having the amino acid sequence of the transmembrane domain of TMEM 141 and a membrane penetrating peptide sequence.

TECHNICAL BACKGROUND

In recent years, a relationship between Hedgehog signaling pathway and a carcinogenic mechanism or cancer stem cells has gotten a lot of attention. For example, with regard to the relationship between sonic hedgehog (SHH), which is one of the hedgehog ligands playing important roles in embryogenesis in mammals, and PTCH1 as a receptor for SHH, PTCH1 in the absence of SHH suppresses smoothened (SMO) as a transmembrane protein to suppress signal transduction. On the other hand, when SHH binds to PTCH1, signal transduction occurs according to the pathway as caused by operation of activated SMO. Furthermore, as the Gli transcription factors are induced, an occurrence of various physiological phenomena is caused. In this regard, reference can be made to Cancers, Vol. 7, 2015, pp. 1333-1348.

With regard to the carcinogenesis, activation of SMO, that is, activation of the hedgehog signal transduction, is recognized from tissues of various tumors. Meanwhile, it is known that proliferation or invasive property of cancer cells can be inhibited by suppressing the activation of SMO. For example, cyclopamine is known as an inhibitor for SMO, and it receives an attention as a therapeutic candidate for tumor (cancer) in which Hedgehog signaling pathway is overexpressed. For example, in WO 2013/186934, a synthetic peptide consisting of total 16 amino acid residues, which is expected to have an interaction with PTCH1, is disclosed, and it is also described that the synthetic peptide has an inhibitory effect on proliferation of human pancreatic cancer cells.

SUMMARY OF THE INVENTION

The present invention is devised under the subject (object) of providing a new anti-tumor (anti-cancer) synthetic peptide which has a constitution different from conventionally known constitutions (for example, amino acid sequence).

The inventors of the present invention focused on the fact that SMO or PTCH1 related to Hedgehog signaling pathway is a transmembrane protein. Furthermore, it was surprisingly found that a synthetic peptide in which the amino acid sequence constituting the transmembrane domain of transmembrane protein 141 (TMEM 141), which is one of transmembrane proteins with a function not yet well known, is combined with an amino acid sequence constituting a conventionally known cell penetrating peptide (CPP) has an excellent anti-tumor (anti-cancer) property against various tumor cells, and thus present invention is completed accordingly.

Namely, the synthetic peptide disclosed herein is an anti-tumor peptide which is capable of inhibiting at least one type of tumor cells. Furthermore, the synthetic peptide has both amino acid sequences represented by the following (1) and (2):

(1) an amino acid sequence constituting the transmembrane domain of transmembrane protein 141 (TMEM 141), or a modified amino acid sequence having deletion, replacement, or addition of one or more (for example, two or three) amino acid residues of the amino acid sequence; and (2) an amino acid sequence functioning as a cell membrane penetrating peptide (CPP).

Preferably, the total number of amino acid residues of the anti-tumor peptide disclosed herein is 100 or less. From the viewpoint of cost related to production, easiness for synthesis, and handlability, the total amino acid residue number is more preferably 80 or less (for example, 70 or less).

Alternatively, a synthetic peptide in which the amino acid sequence represented in the above (1) and the amino acid sequence represented in the above (2) correspond to 80% by number or more (more preferably, 90% by number or more, for example, 100% by number) of the total is one preferred aspect of the anti-tumor peptide disclosed herein.

According to one preferred aspect of the anti-tumor peptide disclosed herein, the amino acid sequence constituting the transmembrane domain of TMEM 141 is represented by any one of SEQ ID NOs: 1 to 10.

Furthermore, according to other preferred aspect of the anti-tumor peptide disclosed herein, the amino acid sequence functioning as the CPP is polyarginine (typically consisting of 5 or more and 9 or less arginine residues), an amino acid sequence represented by any one of SEQ ID NOs: 11 to 28, or a modified amino acid sequence functioning as a CPP which and having deletion, replacement, or addition of one or more (for example, two or three) amino acid residues of the amino acid sequence.

For example, a synthetic peptide having both of the followings can be mentioned as a preferred example:

(i) an amino acid sequence represented by any one of SEQ ID NOs: 1 to 10, or a modified amino acid sequence which has deletion, replacement, or addition of one or more (for example, two or three) amino acid residues of the amino acid sequence; and (ii) polyarginine, an amino acid sequence represented by any one of SEQ ID NOs: 11 to 28, or a modified amino acid sequence functioning as a CPP and having deletion, replacement, or addition of one or more (for example, two or three) amino acid residues of the amino acid sequence.

The synthetic peptide having an amino acid sequence represented by any one of SEQ ID NOs: 29 to 40 is a preferred specific example.

The present invention further provides an anti-tumor composition for inhibiting proliferation of at least one type of tumor cells having any synthetic peptide (anti-tumor peptide) disclosed herein and at least one pharmaceutically acceptable carrier.

By containing the anti-tumor peptide disclosed herein, the composition can be used as an anti-tumor preparation (in other words, anti-cancer preparation) or as a material for developing a new anti-tumor preparation (in other words, anti-cancer preparation).

The present invention further provides a method for inhibiting proliferation of at least one type of tumor cells, the method including supplying (for example, outside of a living body=in vitro, or inside of a living body=in vivo) at least once any synthetic peptide (anti-tumor peptide) disclosed herein to a tumor cell as a subject.

According to the method with above constitution, as the anti-tumor peptide disclosed herein is supplied to a tumor cell, proliferation of the tumor cell (further, enlargement of tumors, cancer tissues) can be suppressed or inhibited.

DESCRIPTION OF THE PREFERRED EMBODIMENTS

Hereinbelow, preferred embodiments of the present invention are explained. The items, which are other than those particularly described in the specification (for example, primary structure or chain length of a synthetic peptide described herein), and the items required for carrying out the present invention (general items such as a method for chemical synthesis of a peptide, technique for cell culture, and preparation of a pharmaceutical composition containing peptide as a component) can be recognized as items to be designed by a person skilled in the pertinent art based on conventional techniques in the field of cell engineering, physiology, medicine, pharmacology, organic chemistry, biochemistry, genetic engineering, protein engineering, molecular biology, genetics, or the like. The present invention can be carried out based on the content described in the specification and common technical idea in the pertinent art. Furthermore, in the explanations that are given below, the amino acid is represented by single-letter description depending on a case (with the proviso that, three-letter description is used in Sequence Listing).

All contents of the every literature cited in the specification are incorporated by reference herein in their entirety.

In the specification, the "tumor" is a term which is interpreted in broad sense, and it indicates carcinoma and sarcoma, or general tumors (typically, malignant tumors) including lesions in blood or hematopoietic tissues (for example, leukemia and lymphoma).

Furthermore, the "tumor cell" has the same meaning as "cancer cell", and it indicates a cell for forming tumor, and typically a cell showing abnormal proliferation irrelevant of normal tissues in neighborhood (that is, transformed cell). Thus, unless specifically described otherwise, if it is a cell categorized not as a normal cell but as a tumor cell (cancer cell), it is referred to as a tumor cell regardless of the origin or property of the cell. Cells constituting epithelial tumor (squamous cell carcinoma, adenocarcinoma, or the like), non-epithelial tumor (various kinds of sarcoma, osteosarcoma, or the like), various kinds of blastoma (neuroblastoma, retinoblastoma, or the like), lymphoma, melanoma or the like may be included in the tumor cell which is described herein.

Furthermore, the "synthetic peptide" described in the specification indicates a peptide fragment of which peptide chain is not independently present in stable form in nature but produced by artificial chemical synthesis or biosynthesis (that is, production based on genetic engineering), and can be stably present in a certain composition. Herein, the "peptide" is a term indicating a polymer of amino acids having plural peptide bonds. Although it is not limited by the number of amino acid residues included in a peptide chain, it typically indicates those with relatively small molecular weight, for example, a peptide of which total number of amino acid residues is 100 or less, in general (preferably 80 or less, for example, 70 or less).

Furthermore, in the specification, unless specifically described otherwise, the "amino acid residue" is a term which includes an N-terminal amino acid and a C-terminal amino acid of a peptide chain.

Furthermore, with regard to the amino acid sequence described in the specification, the left side always indicates an N-terminal side while the right side always indicates a C-terminal side.

In the specification, the "modified amino acid sequence" regarding a certain amino acid sequence indicates an amino acid sequence that is formed by having deletion, replacement, or addition (insertion) of one or several (typically 9 or less, and preferably 5 or less) amino acid residues, for example, one, two, or three amino acid residues without impairing the function owned by the certain amino acid sequence (for example, anti-tumor activity or cell penetrating activity). For example, a sequence generated based on so-called conservative amino acid replacement in which one, two, or three amino acid residues are replaced in conservative manner (for example, a sequence in which a basic amino acid residue is replaced with other basic amino acid residue: for example, mutual replacement between lysine residue and arginine residue), or a sequence generated based on addition (insertion) or deletion of one, two, or three amino acid residues of a certain amino acid sequence are the typical examples that are included in the modified amino acid sequence described in the specification. As such, the anti-tumor peptide disclosed herein with the examples include, in addition to a synthetic peptide consisting of the same amino acid sequence as the amino acid sequence of each sequence number, a synthetic peptide which has a modified amino acid sequence in which one, two, or three amino acid residues of the amino acid sequence of each sequence number are replaced (for example, conservative amino acid replacement described above), deleted, or added, and consists of an amino acid sequence also exhibiting the anti-tumor activity.

The artificially synthesized anti-tumor peptide disclosed herein is a short chain peptide which is not present in nature, and it is a peptide having both kinds of the above amino acid sequence, that is:

(1) an amino acid sequence constituting the transmembrane domain of TMEM 141, or a modified amino acid sequence having deletion, replacement, or addition of one or more (for example, two or three) amino acid residues of the amino acid sequence; and (2) an amino acid sequence functioning as a CPP.

Transmembrane protein 141 (TMEM 141) is a membrane protein which typically consists of approximately 100 to 130 amino acid residues, and the function of TMEM 141 is not known well. The gene encoding TMEM 141 is conserved not only in human but also in chimpanzee, cow, dog, mouse, rat, chicken, zebrafish or the like, and the ortholog of the human TMEM 141 gene is found in at least 100 biospecies.

The information relating to TMEM 141 gene and the information relating to the amino acid sequence thereof can be obtained from knowledge base (database) of various official international organizations. For example, the entire amino acid sequence information and information of the transmembrane domain of TMEM 141 originating various biospecies (including amino acid sequence) can be obtained from Universal Protein Resource (UniProt). Alternatively, based on the information of TMEM 141 gene or the information of amino acid sequence of TMEM 141, the transmembrane domain of TMEM 141 can be easily identified by a tool such as TMHMM and SOSUI.

Although it is not particularly limited, preferred examples of the transmembrane domain of TMEM 141 are shown in SEQ ID NOs: 1 to 10. Specifically, they are as described hereinbelow.

SEQ ID NO: 1 is a transmembrane domain which consists of total 21 amino acid residues from the 32nd to 52nd of human TMEM 141.

SEQ ID NO: 2 is a transmembrane domain which consists of total 21 amino acid residues from the 58th to 78th of human TMEM 141.

SEQ ID NO: 3 is a transmembrane domain which consists of total 19 amino acid residues from the 34th to 52nd of cow TMEM 141.

SEQ ID NO: 4 is a transmembrane domain which consists of total 17 amino acid residues from the 62nd to 78th of cow TMEM 141.

SEQ ID NO: 5 is a transmembrane domain which consists of total 20 amino acid residues from the 29th to 48th of zebrafish TMEM 141.

SEQ ID NO: 6 is a transmembrane domain which consists of total 19 amino acid residues from the 60th to 78th of zebrafish TMEM 141.

SEQ ID NO: 7 is a transmembrane domain which consists of total 23 amino acid residues from the 30th to 52nd of mouse TMEM 141.

SEQ ID NO: 8 is a transmembrane domain which consists of total 20 amino acid residues from the 59th to 78th of mouse TMEM 141.

SEQ ID NO: 9 is a transmembrane domain which consists of total 22 amino acid residues from the 32nd to 53rd of Japanese rice fish TMEM 141.

SEQ ID NO: 10 is a transmembrane domain which consists of total 21 amino acid residues from the 58th to 78th of Japanese rice fish TMEM 141.

As for the amino acid sequence which functions as a CPP used for constructing an anti-tumor peptide described herein, various kinds of CPP that are conventionally known can be employed. For example, a so-called polyarginine Rn consisting of 3 or more, preferably 5 or more and 11 or less, and preferably 9 or less arginine residues is suitable as CPP used herein.

Other than that, various kinds of CPP can be also employed.

Although it is not particularly limited, preferred examples of CPP are shown in SEQ ID NOs: 11 to 28. Specifically, they are as described hereinbelow.

The amino acid sequence of SEQ ID NO: 11 corresponds to nucleolar localization signal (NoLS) which consists of total 14 amino acid residues derived from basic fibroblast growth factor (FGF2).

The amino acid sequence of SEQ ID NO: 12 corresponds to NoLS which consists of total 19 amino acid residues derived from one kind of nucleolar proteins (ApLLP).

The amino acid sequence of SEQ ID NO: 13 corresponds to NoLS which consists of total 16 amino acid residues derived from protein (y (1) 34.5) of herpes simplex virus type 1 (HSV-1).

The amino acid sequence of SEQ ID NO: 14 corresponds to NoLS which consists of total 19 amino acid residues derived from p40 protein of human I-mfa domain-containing protein (HIC).

The amino acid sequence of SEQ ID NO: 15 corresponds to NoLS which consists of total 16 amino acid residues derived from MEQ protein of Marek disease virus (MDV).

The amino acid sequence of SEQ ID NO: 16 corresponds to NoLS which consists of total 17 amino acid residues derived from survivin-deltaEx3, which is a protein for inhibiting apoptosis.

The amino acid sequence of SEQ ID NO: 17 corresponds to NoLS which consists of total 7 amino acid residues derived from angiogenin, which is a vascular growth factor.

The amino acid sequence of SEQ ID NO: 18 corresponds to NoLS which consists of total 8 amino acid residues derived from MDM2, which is a nuclear phosphoprotein MDM2 forming a complex with p53 tumor suppressor protein.

The amino acid sequence of SEQ ID NO: 19 corresponds to NoLS which consists of total 9 amino acid residues derived from GGNNVα, which is a protein of betanoda virus.

The amino acid sequence of SEQ ID NO: 20 corresponds to NoLS which consists of total 7 amino acid residues derived from NF-κB inducing kinase (NIK).

The amino acid sequence of SEQ ID NO: 21 corresponds to NoLS which consists of total 15 amino acid residues derived from nuclear VCP-like protein.

The amino acid sequence of SEQ ID NO: 22 corresponds to NoLS which consists of total 18 amino acid residues derived from p120, which is a nucleolar protein.

The amino acid sequence of SEQ ID NO: 23 corresponds to NoLS which consists of total 14 amino acid residues derived from ORF57 protein of herpes virus saimiri (HVS).

The amino acid sequence of SEQ ID NO: 24 corresponds to NoLS which consists of total 13 amino acid residues from the 491st amino acid residues to 503rd amino acid residue of LIM kinase 2, which is one kind of protein kinases involved with intracellular information transfer and present in human endothelial cells.

The amino acid sequence of SEQ ID NO: 25 corresponds to NoLS which consists of total 8 amino acid residues included in N protein (nucleocapsid protein) of avian infectious bronchitis virus (IBV).

The amino acid sequence of SEQ ID NO: 26 corresponds to a membrane penetrating motif which consists of total 11 amino acid sequence derived from a domain introduced with a protein included in TAT of human immunodeficiency virus (HIV).

The amino acid sequence of SEQ ID NO: 27 corresponds to a membrane penetrating motif which consists of total 11 amino acid sequence derived from a domain (PTD4) introduced with a protein obtained by modification of TAT above.

The amino acid sequence of SEQ ID NO: 28 corresponds to a membrane penetrating motif which consists of total 18 amino acid sequence derived from ANT of Antennapedia, which is a variant of *Drosophila*.

Among them, the amino acid sequence relating to NoLS (or modified amino acid sequence thereof) is particularly preferable. For example, the CPP sequence relating to NoLS as represented by SEQ ID NO: 24 or SEQ ID NO: 25 can be suitably used for constructing the anti-tumor peptide described herein.

It is preferable that the peptide chain (amino acid sequence) of an anti-tumor peptide described herein has (1) the amino acid sequence constituting the transmembrane domain of TMEM 141 or a modified amino acid sequence thereof (hereinbelow, also described as "TMEM 141 related sequence"), and (2) an amino acid sequence functioning as a CPP (hereinbelow, also described as "CPP related sequence"), and it is also possible that any one of the TMEM 141 related sequence and CPP related sequence is present relatively at N-terminal side (C-terminal side).

It is preferable that the TMEM 141 related sequence and CPP related sequence are present such that they are substantially close to each other. Specifically, it is preferable that an amino acid residue not included in the TMEM 141 related sequence and CPP related sequence is not present between those sequences, or even if it is present, the number of the amino acid residue is preferably 10 or less (more preferably 5 or less).

As long as the anti-tumor activity for inhibiting proliferation of at least one type of tumor cells is not lost, a sequence (amino acid residue) other than the amino acid sequence constituting the TMEM 141 related sequence and CPP related sequence may be included.

Herein, with regard to the disclosed anti-tumor peptide, the number of the total amino acid residues constituting the peptide chain is suitably 100 or less. It is preferably 80 or less, and preferably 70 or less (for example, a peptide chain with 25 to 50 residues or so). A peptide with such short length chain can be easily synthesized by chemical method and can easily provide an anti-tumor peptide. Although it is not particularly limited, a linear-chain or helix-shaped peptide is preferable from the viewpoint that it hardly becomes an immunogen (antigen). A peptide with such shape hardly forms an epitope.

Ratio of the TMEM 141 related sequence and the CPP related sequence relative to the total amino acid sequence of a synthesized peptide is not particularly limited as long as the anti-tumor activity is not lost. However, the ratio is preferably 80% by number or more, and more preferably 90% by number or more, in general. Furthermore, it is preferable that all amino acid residues are an L-form amino acid. However, as long as the anti-tumor activity is not lost, it is also possible that part or all of the amino acid residues are replaced with a D-form amino acid.

Preferably, it is preferable that at least one amino acid residue of the anti-tumor peptide disclosed herein is amidated. According to amidation of a carboxyl group of an amino acid residue (typically, C-terminal amino acid residue of a peptide chain), the structural stability of a synthetic peptide (for example, resistance to protease) can be enhanced.

The anti-tumor peptide disclosed herein can be easily synthesized in view of a general method for chemical synthesis. For example, any one of conventionally known solid phase synthetic method and liquid phase synthetic method can be adopted. A solid phase synthetic method in which t-butyloxycarbonyl (Boc) or 9-fluorenylmethoxycarbonyl (Fmoc) is applied as a protective group for an amino group is appropriate.

As for the anti-tumor peptide disclosed herein, a peptide chain having desired amino acid sequence, modified (for example, C-terminal amidation or the like) portion can be synthesized by a solid phase synthetic method using a commercially available peptide synthesizer.

Alternatively, the anti-tumor peptide can be obtained by biosynthesis based on genetic engineering techniques. Namely, a polynucleotide (typically, DNA) of a nucleotide sequence (including ATG initiation codon) encoding the amino acid sequence of a desired anti-tumor peptide is synthesized. Then, a recombinant vector having a gene construct for expression, which consists of the synthesized polynucleotide (DNA) and various regulation elements (including promoter, ribosome binding site, terminator, enhancer, and various cis elements for controlling expression level) for expressing the amino acid sequence in a host cell, is constructed in accordance with a host cell.

According to a general technique, the recombinant vector is introduced to a host cell (for example, yeast, insect cells, and plant cells), and the host cells, or tissues or individuals containing the cells are cultured at predetermined conditions. Accordingly, the desired peptide can be expressed and produced in cells. Then, the peptide is isolated from the host cells (or, when the peptide is secreted, isolated from a medium), and by performing refolding, purification, or the like, if necessary, the desired anti-tumor peptide can be obtained.

Furthermore, as for the method for constructing a recombinant vector, a method for introducing a constructed recombinant vector to a host cell, or the like, it is sufficient to directly adopt methods that are conventionally carried out in the field, and because the present invention is not characterized by those methods themselves, detailed explanations therefor are omitted.

Alternatively, a desired polypeptide can be obtained by in vitro synthesis by constructing a template DNA for cell-free protein synthesis system (that is, synthesized gene fragment containing a nucleotide sequence encoding the amino acid sequence of the anti-tumor peptide), using various kinds of chemical compounds that are required for peptide synthesis (for example, ATP, RNA polymerase, and amino acids), and employing a so-called cell-free protein synthesis system. With regard to the cell-free protein synthesis system, reference can be made to the paper by Shimizu, et al. (Shimizu et al., Nature Biotechnology, 19, 751-755 (2001)) and the paper by Madin et al. (Madin et al., Proc. Natl. Acad. Sci. USA, 97 (2), 559-564 (2000)). Based on the techniques described in those papers, many companies already perform contract manufacturing of a polypeptide, and also a kit for cell-free protein synthesis is currently commercially available (for example, it can be obtained from CellFree Sciences Co., Ltd. in Japan).

The single-stranded or double-stranded polynucleotide including a nucleotide sequence encoding the anti-tumor peptide disclosed herein and/or a nucleotide sequence complementary to that nucleotide sequence can be easily produced (synthesized) by a conventionally known method. Namely, by selecting a codon which corresponds to each amino acid reside constituting a designed amino acid sequence, a nucleotide sequence corresponding to the amino acid sequence of an anti-tumor peptide is easily decided and provided. Furthermore, once the nucleotide sequence is decided, a polynucleotide (single-stranded) corresponding to a desired nucleotide sequence can be easily obtained by using a DNA synthesizer or the like. Furthermore, by using the obtained single-stranded DNA as a template and employing various kinds of enzyme synthesis means (typically, PCR), a desired double-stranded DNA can be obtained. Furthermore, the polynucleotide can have either DNA form or RNA (mRNA or the like) form. A DNA can be provided as a single strand or a double strand. When a DNA is provided as a single strand, it may be either a coding chain (sense chain) or a non-coding chain (anti-sense chain) that is complementary to the coding chain.

The polynucleotide obtained according to above can be used, as described before, as a material for constructing a recombinant gene (expression cassette) for production of an anti-tumor peptide in various kinds of host cells or a cell-free protein synthesis system.

The anti-tumor peptide disclosed herein can be suitably used as an effective ingredient of a composition which is used for inhibiting (or suppressing) proliferation of tumor cells (that is, a pharmaceutical anti-tumor composition such as an anti-tumor preparation).

Furthermore, the anti-tumor peptide may be in salt form as long as the anti-tumor activity is not lost. For example, an acid addition salt of a synthetic peptide, which can be obtained by addition reaction of a typically used inorganic acid or an organic acid, can be used. As such, the "peptide" described in the specification and claims include those in salt form.

The anti-tumor composition disclosed herein may include, as long as the anti-tumor activity of an anti-tumor peptide as an effective ingredient is not lost, various kinds of a pharmaceutically acceptable carrier, depending on the form of use. For example, a carrier generally used as a diluent, a vehicle, or the like in peptide medicines can be applied.

Although it may suitably vary depending on the use or form of an anti-tumor composition described herein, typical examples of the carrier include water, physiological saline, and various kinds of an organic solvent. It may be also an aqueous solution of alcohol (ethanol or the like) at suitable concentration, glycerol, or non-drying oil such as olive oil. It may be also a liposome. Furthermore, examples of a secondary component which may be included in the anti-tumor composition include various kinds of a filler, a bulking agent, a binding agent, a moisturizing agent, a surfactant, a colorant, and a fragrance.

Typical examples of the form of the anti-tumor composition (anti-tumor preparation) include a liquid preparation, a suspension, an oil preparation, an aerosol, a foaming agent, a granule, a powder, a tablet, a capsule, an ointment, and an aqueous gel preparation. Furthermore, as it is used for injection or the like, it can be prepared as a freeze-dried product or a granulated product which is dissolved immediately before use in physiological saline or suitable buffer solution (for example, PBS) to give a pharmaceutical solution.

Furthermore, the process itself for preparing a composition (pharmaceutical preparation) in various forms by using the anti-tumor peptide (main component) and various kinds of a carrier (minor component) can be based on a conventionally known method. Because the present invention is not characterized by such production method itself, detailed explanations therefor are omitted herein. As a source of information regarding the formulation, mention can be made to Comprehensive Medicinal Chemistry, edited by Corwin Hansch, published by Pergamon Press (1990), for example. The content of this book is incorporated by reference herein in its entirety.

Cells as a subject for application of the anti-tumor composition (anti-tumor peptide) disclosed herein are not particularly limited, as long as they are tumor cells (cancer cells), and the anti-tumor composition can be applied to various types of tumor cells occurring in human or mammals other human. Examples thereof include cells forming squamous cell carcinoma or cells forming adenocarcinoma, for example, cancer cells of breast cancer, pancreatic cancer, prostate cancer, or lung cancer, and cells forming neuroblastoma, retinoblastoma, pheochromocytoma, and other cytoma.

The anti-tumor composition disclosed herein may be used, similar to a conventional peptide preparation, according to a method or a dosage depending on the form and object of the composition. For example, as a liquid preparation, it can be administered in a desired amount to an affected area (typically, tissue of malignant tumor) of a patient (that is, living body) by intravenous, intramuscular, subcutaneous, intradermal, or intraperitoneal injection. Alternatively, the composition in solid form such as a tablet or in gel phase or aqueous gel form such as an ointment can be directly administered to a certain tissue (that is, affected area such as tissues or organs containing tumor cells). Alternatively, the composition in solid form such as a tablet can be orally administered. In case of oral administration, it is preferable to have capsulation or application of a protective (coating) material to inhibit the decomposition by digestive enzymes in digestive tract.

Alternatively, it is possible that, to tumor cells (including cell mass, tissues, or organs removed from a living body) cultured outside a living body (in vitro), a suitable amount of the anti-tumor composition disclosed herein (that is, suitable amount of the anti-tumor peptide) is supplied at least once to a medium of culture cells (tissues or the like) as a subject. The supply amount per supply and supply number are not particularly limited, as they may vary depending on conditions such as the type of tumor cells to be cultured, the cell density (cell density at the time of starting culture), the number of subculture, the culture conditions and the type of a medium. However, it is preferable that the anti-tumor composition is added once or several times such that the concentration of the anti-tumor peptide in a medium is generally in the range of 25 µM to 200 µM, and preferably in the range of 50 µM to 100 µM.

Hereinbelow, several examples relating to the present invention are explained. However, it is not intended to limit the present invention to those expressed by the examples.

TABLE 1

| Sample No. | Amino acid sequence | Total amino acid residue number |
|---|---|---|
| 1 | MKGTGTFLLGTAGLFTLQKVTKKRTLRKNDRK KR-$_{CONH2}$ (SEQ ID NO: 29) | 34 |
| 2 | MKGTGTFLLGIAGLFTLQKVIQRRRRRRRR R-$_{CONH2}$ (SEQ ID NO: 30) | 31 |
| 3 | YPLQWNLLISILASSVGSYAVKKRTLRKNDRK KR-$_{CONH3}$ (SEQ ID NO: 31) | 34 |
| 4 | MKGYFTFVTGTGMAFGLQMFIKKRTLRKNDRK KR-$_{CONH2}$ (SEQ ID NO: 32) | 34 |
| 5 | YPLQWSLLVAVVAGSVVSYGVKKRTLRKNDRK KR-$_{CONH2}$ (SEQ ID NO: 33) | 34 |
| 6 | GVSTFVTGTGATFGLQMLVRRRRRR-$_{CONH2}$ (SEQ ID NO: 34) | 25 |
| 7 | WKVLLAVVAGSVASYWVRRRRRR-$_{CONH2}$ (SEQ ID NO: 35) | 23 |
| 8 | YAFMKGTASFILGTVGIFFGWRRQARFK-$_{CONH2}$ (SEQ ID NO: 36) | 28 |
| 9 | LQWNLFVSIVSSSVFSYSVWRRQARFK-$_{CONH2}$ (SEQ ID NO: 37) | 27 |
| 10 | AFMKGVFTFVTGTGATFGLLMFTRRRRRR-$_{CONH2}$ (SEQ ID NO: 38) | 29 |
| 11 | PVQWSFLVSAIAGSVASYRVWRRQARFK-$_{CONH2}$ (SEQ ID NO: 39) | 28 |
| 12 | RRRMKGVFTFVTGTGMAFGLQMFIQRKFPYPL QW-SLLVAVVAGSVVSYGRRRRR-$_{CONH2}$ (SEQ ID NO: 40) | 54 |
| 13 | YPLQWSLLVAVVAGSVVSYGVTRVESE-$_{CONH2}$ (SEQ ID NO: 41) | 27 |

Test Example 1: Synthesis of Peptide

Total 13 kinds of peptide shown in Table 1 were prepared by using a commercially available peptide synthesizer. Specifics are as described below.

Sample 1 is a synthetic peptide which includes total 21 amino acid residues from the 32nd to 52nd of Japanese rice fish TMEM 141 as the TMEM 141 related sequence, and the amino acid sequence of SEQ ID NO: 24 (NoLS of LIM kinase 2) as the CPP related sequence at the C-terminal side of the TMEM 141 related sequence.

Sample 2 is a synthetic peptide which includes total 22 amino acid residues from the 32nd to 53rd of Japanese rice fish TMEM 141 as the TMEM 141 related sequence, and 9 arginine residues (polyarginine) as the CPP related sequence at the C-terminal side of the TMEM 141 related sequence.

Sample 3 is a synthetic peptide which includes total 21 amino acid residues from the 58th to 78th of Japanese rice fish TMEM 141 as the TMEM 141 related sequence, and the amino acid sequence of SEQ ID NO: 24 as the CPP related sequence at the C-terminal side of the TMEM 141 related sequence.

Sample 4 is a synthetic peptide which includes total 21 amino acid residues from the 32nd to 52nd of human TMEM 141 as the TMEM 141 related sequence, and the amino acid sequence of SEQ ID NO: 24 as the CPP related sequence at the C-terminal side of the TMEM 141 related sequence.

Sample 5 is a synthetic peptide which includes total 21 amino acid residues from the 58th to 78th of human TMEM 141 as the TMEM 141 related sequence, and the amino acid sequence of SEQ ID NO: 24 as the CPP related sequence at the C-terminal side of the TMEM 141 related sequence.

Sample 6 is a synthetic peptide which includes total 19 amino acid residues from the 34th to 52nd of cow TMEM 141 as the TMEM 141 related sequence, and 6 arginine residues (polyarginine) as the CPP related sequence at the C-terminal side of the TMEM 141 related sequence.

Sample 7 is a synthetic peptide which includes total 17 amino acid residues from the 62nd to 78th of cow TMEM 141 as the TMEM 141 related sequence, and 6 arginine residues (polyarginine) as the CPP related sequence at the C-terminal side of the TMEM 141 related sequence.

Sample 8 is a synthetic peptide which includes total 20 amino acid residues from the 29th to 48th of zebrafish TMEM 141 as the TMEM 141 related sequence, and the amino acid sequence of SEQ ID NO: 25 (NoLS of N protein of IBV) as the CPP related sequence at the C-terminal side of the TMEM 141 related sequence.

Sample 9 is a synthetic peptide which includes total 19 amino acid residues from the 60th to 78th of zebrafish TMEM 141 as the TMEM 141 related sequence, and the amino acid sequence of SEQ ID NO: 25 as the CPP related sequence at the C-terminal side of the TMEM 141 related sequence.

Sample 10 is a synthetic peptide which includes total 23 amino acid residues from the 30th to 52nd of mouse TMEM 141 as the TMEM 141 related sequence, and 6 arginine residues (polyarginine) as the CPP related sequence at the C-terminal side of the TMEM 141 related sequence.

Sample 11 is a synthetic peptide which includes total 20 amino acid residues from the 59th to 78th of mouse TMEM 141 as the TMEM 141 related sequence, and the amino acid sequence of SEQ ID NO: 25 as the CPP related sequence at the C-terminal side of the TMEM 141 related sequence.

Sample 12 is a synthetic peptide which includes 3 arginine residues (polyarginine) at the N-terminal side, total 46 amino acid residues from the 32nd to 77th of human TMEM 141 at the C-terminal side, and also 5 arginine residues (polyarginine) as the CPP related sequence at the C-terminal side. Namely, the synthetic peptide of sample 12 has, as the TMEM 141 related sequence, a sequence consisting of total 21 amino acid residues from the 32nd to 52nd of human TMEM 141, and also a sequence consisting of total 20 amino acid residues from the 58th to 77th of human TMEM 141.

Furthermore, sample 13 prepared as a comparative example is a synthetic peptide which consists of total 27 amino acid residues from the 58th to 84th of human TMEM 141. Namely, the synthetic peptide of sample 13 does not have a CPP related sequence.

All the peptides of above sample 1 to sample 13 were synthesized by carrying out, according to the manual, solid phase synthesis (Fmoc method) using a commercially available peptide synthesizer. Furthermore, because the present invention is not characterized by a mode of using a peptide synthesizer itself, detailed explanations therefor are omitted herein. Furthermore, for all synthetic peptides, the carboxyl group (—COOH) at C-terminal amino acid is amidated (—$CONH_2$).

The synthesized peptide of each sample was dissolved in dimethyl sulfoxide (DMSO) to prepare a stock solution of each sample peptide.

Test Example 2: Test for Evaluating Anti-Tumor Activity of Each Synthetic Peptide For any one of each sample peptide synthesized in the above Test Example 1, an anti-tumor activity was evaluated by having various kinds of cultured tumor cells as a subject.

Specifically, as a tumor cell for test, cultured mammary cancer cell line (MCF-7), cultured mammary cancer cell line (MDA-MB-231), cultured pancreatic cancer cell line (MIA PaCa-2), cultured prostate cancer cell line (PC-3), and cultured prostate cancer cell line (DU-145), which are currently available on the market, were used. Furthermore, as a subject for comparison, commercially available cultured cell line of normal human mammary epithelial cells was used. Details of the test are described below.

Namely, those cell lines were cultured in advance in DMEM medium (that is, Dulbecco's MEM medium (DMEM medium: product of Gibco) containing 10% fetal bovine serum (FBS: product of Gibco), 2 mM L-glutamine, 50 unit/mL penicillin, and 50 μg/mL of streptomycin), and adjusted such that the number of cells per well of a 96-hole (well) plate is about $1 \times 10^4$. The medium amount was 100 μL per well.

Subsequently, the 96-hole (well) plate was kept in a $CO_2$ incubator and pre-incubation was carried out for about 1 day (22 hours to 23 hours) at conditions of 37° C., 5% $CO_2$.

After that, a test medium containing the peptide at each concentration was prepared such that the peptide concentration in any sample to be an evaluation subject is any one of 3.13 μM, 6.25 μM, 12.5 μM, 25 μM, 50 μM, and 100 μM. Then, the test medium was supplied, in an amount of 90 μL per well, to a well in which the cells as an evaluation subject have been cultured (that is, well after the above pre-incubation). In addition, the 96-hole (well) plate was returned to the $CO_2$ incubator and incubated for 5 hours at conditions of 37° C., 5% $CO_2$.

Furthermore, number (n) of the test wells for the test group added with each peptide at each peptide concentration was all set at 3. Thus, the result values shown in the following table correspond to an average value of the results which have been obtained from each of test well number of 3. Cell survival rate (%) was determined as described below.

Upon completion of the incubation for 5 hours described above, the medium in each well was replaced with 100 μL of fresh medium not containing the peptide. Furthermore, "Cell Counting Kit-8" (product of Dojindo Laboratories) containing as a chromogenic reagent "Aqueous tetrazolium salt (WST-8)", which is a reagent for measuring cell proliferation, was added in an amount of 10 μL to each well. After that, the 96-hole (well) plate was returned to the $CO_2$ incubator and incubated for 1.5 hours at conditions of 37° C. 5% $CO_2$.

Upon completion of the incubation, the cell culture solution added with the above reagent was recovered, and simultaneously, according to colorimetry by which absorbance at wavelength of 450 nm based on reduction of tetrazolium salt (value calibrated with absorbance at wavelength of 650 nm: A450-A650), the cell survival rate (%) was evaluated. Specifically, in view of a relative value which is obtained by setting the measurement value (measured absorbance) of a comparative test group, in which the above incubation for 5 hours has been carried out only with a medium not containing any peptide, as the cell survival rate of 100%, the cell survival rate (%) of each test cell line was calculated from the measured absorbance. The results are shown in Table 2 to Table 4.

TABLE 2

Cell survival rate (%)

| Cell line for test | Peptide concentration (μM) | No. 1 SEQ ID NO: 29 | No. 2 SEQ ID NO: 30 | No. 3 SEQ ID NO: 31 | No. 4 SEQ ID NO: 32 | No. 5 SEQ ID NO: 33 |
|---|---|---|---|---|---|---|
| Normal human mammary epithelial cells | 12.5 | 115.8 | 88.3 | 83.6 | 99.2 | 97.5 |
| | 25 | 94 | 82.1 | 71.6 | 90.5 | 90.2 |
| | 50 | 68.2 | 56.1 | 81.5 | 62 | 97.7 |
| | 100 | 34.6 | 42.7 | 74.8 | 35.6 | 98.3 |
| Mammary cancer cells (MCF-7) | 12.5 | 109.4 | 75.7 | 79.3 | 97.4 | 68.4 |
| | 25 | 100.4 | 49.1 | 71.8 | 80.8 | 66.7 |
| | 50 | 34.3 | 20.2 | 50 | 35.7 | 45.4 |
| | 100 | 20.8 | 17.6 | 32.8 | 18.5 | 36 |
| Mammary cancer cells (MDA-MB-231) | 12.5 | 99.1 | 80 | 77.9 | 110.6 | 76.1 |
| | 25 | 96.6 | 69.7 | 65.7 | 97.2 | 65.1 |
| | 50 | 59.4 | 52.6 | 54.5 | 56.3 | 67.2 |
| | 100 | 26.6 | 44.3 | 45 | 25.7 | 50.2 |
| Pancreatic cancer cells (MIA-PaCa-2) | 12.5 | 86.9 | 94.4 | 101.4 | 132.5 | 79.9 |
| | 25 | 94.6 | 91.3 | 93.8 | 114.9 | 86.4 |
| | 50 | 47.4 | 36.7 | 88.5 | 64.5 | 83.2 |
| | 100 | 15.3 | 7 | 45.6 | 10.3 | 70.1 |
| Prostate cancer cells (PC-3) | 12.5 | 84.3 | 101.1 | 64.6 | 78.8 | 67.9 |
| | 25 | 74 | 80.9 | 66.5 | 66.5 | 66.3 |
| | 50 | 49.7 | 45.2 | 62.5 | 53 | 59.7 |
| | 100 | 25 | 42.6 | 47 | 35.4 | 49.8 |
| Prostate cancer cells (DU-145) | 12.5 | 86.4 | 86.2 | 78.6 | 86.8 | 91.7 |
| | 25 | 66.8 | 75.2 | 73.7 | 73.8 | 85.9 |
| | 50 | 42.2 | 41.2 | 49.3 | 39 | 64 |
| | 100 | 11.1 | 16.4 | 37.5 | 15.4 | 48.9 |

TABLE 3

Cell survival rate (%)

| Cell line for test | Peptide concentration (μM) | No. 8 SEQ ID NO: 36 | No. 9 SEQ ID NO: 37 | No. 10 SEQ ID NO: 38 | No. 11 SEQ ID NO: 39 |
|---|---|---|---|---|---|
| Mammary cancer cells (MDA-MB-231) | 3.13 | 99 | 99 | 101 | 101 |
| | 50 | 76 | 73 | 62 | 77 |

TABLE 4

Cell survival rate (%)

| Cell line for test | Peptide concentration (μM) | No. 12 SEQ ID NO: 40 | No. 13 SEQ ID NO: 41 |
|---|---|---|---|
| Prostate cancer cells (DU-145) | 3.13 | 101.9 | 104.8 |
| | 6.25 | 100.5 | 97.8 |
| | 12.5 | 88.9 | 96.3 |
| | 25 | 75.9 | 101.3 |
| | 50 | 65.2 | 98.9 |
| | 100 | 50.5 | 101.3 |

As it is evident from the results shown in each table, it is recognized that all of the synthetic peptides of sample 1 (SEQ ID NO: 29) to sample 12 (SEQ ID NO: 40) having both the TMEM 141 related sequence and the CPP related sequence have an excellent anti-tumor activity against at least one type of tumor cells (effect of suppressing the proliferation of tumor cells) compared to sample 13 (SEQ ID NO: 41) as a comparative subject. Those results indicate that the anti-tumor peptide disclosed herein can inhibit the proliferation of human tumor cells.

As described in the above, according to the anti-tumor peptide disclosed herein, the proliferation of tumor cells can be inhibited (or suppressed). For such reasons, by using the anti-tumor peptide that is provided by the present invention, an anti-tumor composition (anti-tumor preparation) for inhibiting the proliferation of at least one type of tumor cells can be provided.

The invention claimed is:

1. A synthetic peptide for inhibiting proliferation of at least one type of tumor cells, the synthetic peptide comprising both amino acid sequences represented by the following (1) and (2):
   (1) an amino acid sequence represented by any one of SEQ ID NOs: 1 and 2; and
   (2) an amino acid sequence represented by SEQ ID NO: 24, wherein the total number of amino acid residues of the synthetic peptide is 100 or less.

2. The synthetic peptide according to claim 1, wherein the synthetic peptide comprises an amino acid sequence represented by any one of SEQ ID NOs: 32 and 33.

3. An anti-tumor composition for inhibiting proliferation of at least one type of tumor cells, the anti-tumor composition comprising:
   a synthetic peptide; and
   at least one pharmaceutically acceptable carrier,
   wherein the synthetic peptide comprises both amino acid sequences represented by the following (1) and (2):
   (1) an amino acid sequence represented by any one of SEQ ID NOs: 1 and 2; and (2) an amino acid sequence represented by SEQ ID NO: 24, and the total number of amino acid residues of the synthetic peptide is 100 or less.

4. The composition according to claim 3, wherein the composition comprises an amino acid sequence represented by any one of SEQ NOs: 32 and 33.

\* \* \* \* \*

UNITED STATES PATENT AND TRADEMARK OFFICE
CERTIFICATE OF CORRECTION

PATENT NO. : 10,829,523 B2
APPLICATION NO. : 15/815453
DATED : November 10, 2020
INVENTOR(S) : Baileykobayashi et al.

It is certified that error appears in the above-identified patent and that said Letters Patent is hereby corrected as shown below:

On the Title Page

In item (65), in "Prior Publication Data", in Column 1, Line 1, "2018", insert
--¶(30) Foreign Application Priority Data
Nov. 18, 2016 (JP) 2016-225236--

In Column 2, under "Other Publications", Line 2, delete "annd" and insert --and-- therefor In the Claims In Column 31, Line 7, in Claim 4, after "SEQ", insert --ID--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 41

<210> SEQ ID NO 1
<211> LENGTH: 21
<212> TYPE: PRT
<213> ORGANISM: Artificial Sequence
<220> FEATURE:

```
<223> OTHER INFORMATION: Synthetic peptide

<400> SEQUENCE: 1

Met Lys Gly Val Phe Thr Phe Val Thr Gly Thr Gly Met Ala Phe Gly
1               5                   10                  15

Leu Gln Met Phe Ile
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Tyr Pro Leu Gln Trp Ser Leu Leu Val Ala Val Val Ala Gly Ser Val
1               5                   10                  15

Val Ser Tyr Gly Val
            20

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide

<400> SEQUENCE: 3

Gly Val Ser Thr Phe Val Thr Gly Thr Gly Ala Thr Phe Gly Leu Gln
1               5                   10                  15

Met Leu Val

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Trp Lys Val Leu Leu Ala Val Val Ala Gly Ser Val Ala Ser Tyr Trp
1               5                   10                  15

Val

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Tyr Ala Phe Met Lys Gly Thr Ala Ser Phe Ile Leu Gly Thr Val Gly
1               5                   10                  15

Ile Phe Phe Gly
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 6

Leu Gln Trp Asn Leu Phe Val Ser Ile Val Ser Ser Ser Val Phe Ser
1               5                   10                  15

Tyr Ser Val

<210> SEQ ID NO 7
<211> LENGTH: 23
<212> TYPE: PRT
<213> ORGANISM: Artificial Sequence
<220> FEATURE:
<223> OTHER INFORMATION: Synthetic peptide

<400> SEQUENCE: 7

Ala Phe Met Lys Gly Val Phe Thr Phe Val Thr Gly Thr Gly Ala Thr
1               5                   10                  15

Phe Gly Leu Leu Met Phe Ile
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Pro Val Gln Trp Ser Phe Leu Val Ser Ala Ile Ala Gly Ser Val Ala
1               5                   10                  15

Ser Tyr Arg Val
            20

<210> SEQ ID NO 9
<211> LENGTH: 22
<212> TYPE: PRT
<213> ORGANISM: Artificial Sequence
<220> FEATURE:
<223> OTHER INFORMATION: Synthetic peptide

<400> SEQUENCE: 9

Met Lys Gly Thr Gly Thr Phe Leu Leu Gly Ile Ala Gly Leu Phe Thr
1               5                   10                  15

Leu Gln Lys Val Ile Gln
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Tyr Pro Leu Gln Trp Asn Leu Leu Ile Ser Ile Leu Ala Ser Ser Val
1               5                   10                  15

Gly Ser Tyr Ala Val
            20

<210> SEQ ID NO 11
<211> LENGTH: 14
<212> TYPE: PRT
<213> ORGANISM: Artificial sequence
<220> FEATURE:
<223> OTHER INFORMATION: Synthetic peptide
```

```
<400> SEQUENCE: 11

Arg Ser Arg Lys Tyr Thr Ser Trp Tyr Val Ala Leu Lys Arg
1               5                   10

<210> SEQ ID NO 12
<211> LENGTH: 19
<212> TYPE: PRT
<213> ORGANISM: Artificial sequence
<220> FEATURE:
<223> OTHER INFORMATION: Synthetic peptide

<400> SEQUENCE: 12

Met Ala Lys Ser Ile Arg Ser Lys His Arg Arg Gln Met Arg Met Met
1               5                   10                  15

Lys Arg Glu

<210> SEQ ID NO 13
<211> LENGTH: 16
<212> TYPE: PRT
<213> ORGANISM: Artificial sequence
<220> FEATURE:
<223> OTHER INFORMATION: Synthetic peptide

<400> SEQUENCE: 13

Met Ala Arg Arg Arg Arg His Arg Gly Pro Arg Arg Pro Arg Pro Pro
1               5                   10                  15

<210> SEQ ID NO 14
<211> LENGTH: 19
<212> TYPE: PRT
<213> ORGANISM: Artificial sequence
<220> FEATURE:
<223> OTHER INFORMATION: Synthetic peptide

<400> SEQUENCE: 14

Gly Arg Cys Arg Arg Leu Ala Asn Phe Gly Pro Arg Lys Arg Arg Arg
1               5                   10                  15

Arg Arg Arg

<210> SEQ ID NO 15
<211> LENGTH: 16
<212> TYPE: PRT
<213> ORGANISM: Artificial sequence
<220> FEATURE:
<223> OTHER INFORMATION: Synthetic peptide

<400> SEQUENCE: 15

Arg Arg Arg Lys Arg Asn Arg Asp Ala Arg Arg Arg Arg Arg Lys Gln
1               5                   10                  15

<210> SEQ ID NO 16
<211> LENGTH: 17
<212> TYPE: PRT
<213> ORGANISM: Artificial sequence
<220> FEATURE:
<223> OTHER INFORMATION: Synthetic peptide

<400> SEQUENCE: 16

Met Gln Arg Lys Pro Thr Ile Arg Arg Lys Asn Leu Arg Leu Arg Arg
1               5                   10                  15

Lys

<210> SEQ ID NO 17
```

```
<211> LENGTH: 7
<212> TYPE: PRT
<213> ORGANISM: Artificial sequence
<220> FEATURE:
<223> OTHER INFORMATION: Synthetic peptide

<400> SEQUENCE: 17

Ile Met Arg Arg Arg Gly Leu
1               5

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

Lys Lys Leu Lys Lys Arg Asn Lys
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Arg Arg Arg Ala Asn Asn Arg Arg Arg
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Arg Lys Lys Arg Lys Lys Lys
1               5

<210> SEQ ID NO 21
<211> LENGTH: 15
<212> TYPE: PRT
<213> ORGANISM: Artificial sequence
<220> FEATURE:
<223> OTHER INFORMATION: Synthetic peptide

<400> SEQUENCE: 21

Lys Arg Lys Gly Lys Leu Lys Asn Lys Gly Ser Lys Arg Lys Lys
1               5                   10                  15

<210> SEQ ID NO 22
<211> LENGTH: 18
<212> TYPE: PRT
<213> ORGANISM: Artificial sequence
<220> FEATURE:
<223> OTHER INFORMATION: Synthetic peptide

<400> SEQUENCE: 22

Ser Lys Arg Leu Ser Ser Arg Ala Arg Lys Arg Ala Ala Lys Arg Arg
1               5                   10                  15

Leu Gly
```

```
<210> SEQ ID NO 23
<211> LENGTH: 14
<212> TYPE: PRT
<213> ORGANISM: Artificial sequence
<220> FEATURE:
<223> OTHER INFORMATION: Synthetic peptide

<400> SEQUENCE: 23

Lys Arg Pro Arg Arg Arg Pro Ser Arg Pro Phe Arg Lys Pro
1               5                   10

<210> SEQ ID NO 24
<211> LENGTH: 13
<212> TYPE: PRT
<213> ORGANISM: Artificial sequence
<220> FEATURE:
<223> OTHER INFORMATION: Synthetic peptide

<400> SEQUENCE: 24

Lys Lys Arg Thr Leu Arg Lys Asn Asp Arg Lys Lys Arg
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Trp Arg Arg Gln Ala Arg Phe Lys
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Tyr Gly Arg Lys Lys Arg Arg Gln Arg Arg Arg
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Tyr Ala Arg Ala Ala Ala Arg Gln Ala Arg Ala
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic peptide

<400> SEQUENCE: 28

Lys Gly Arg Gln Val Lys Val Trp Phe Gln Asn Arg Arg Met Lys Trp
1               5                   10                  15

Lys Lys
```

<210> SEQ ID NO 29
<211> LENGTH: 34
<212> TYPE: PRT
<213> ORGANISM: Artificial Sequence
<220> FEATURE:
<223> OTHER INFORMATION: Synthetic peptide

<400> SEQUENCE: 29

Met Lys Gly Thr Gly Thr Phe Leu Leu Gly Ile Ala Gly Leu Phe Thr
1               5                   10                  15

Leu Gln Lys Val Ile Lys Lys Arg Thr Leu Arg Lys Asn Asp Arg Lys
                20                  25                  30

Lys Arg

<210> SEQ ID NO 30
<211> LENGTH: 31
<212> TYPE: PRT
<213> ORGANISM: Artificial Sequence
<220> FEATURE:
<223> OTHER INFORMATION: Synthetic peptide

<400> SEQUENCE: 30

Met Lys Gly Thr Gly Thr Phe Leu Leu Gly Ile Ala Gly Leu Phe Thr
1               5                   10                  15

Leu Gln Lys Val Ile Gln Arg Arg Arg Arg Arg Arg Arg Arg Arg
                20                  25                  30

<210> SEQ ID NO 31
<211> LENGTH: 34
<212> TYPE: PRT
<213> ORGANISM: Artificial Sequence
<220> FEATURE:
<223> OTHER INFORMATION: Synthetic peptide

<400> SEQUENCE: 31

Tyr Pro Leu Gln Trp Asn Leu Leu Ile Ser Ile Leu Ala Ser Ser Val
1               5                   10                  15

Gly Ser Tyr Ala Val Lys Lys Arg Thr Leu Arg Lys Asn Asp Arg Lys
                20                  25                  30

Lys Arg

<210> SEQ ID NO 32
<211> LENGTH: 34
<212> TYPE: PRT
<213> ORGANISM: Artificial Sequence
<220> FEATURE:
<223> OTHER INFORMATION: Synthetic peptide

<400> SEQUENCE: 32

Met Lys Gly Val Phe Thr Phe Val Thr Gly Thr Gly Met Ala Phe Gly
1               5                   10                  15

Leu Gln Met Phe Ile Lys Lys Arg Thr Leu Arg Lys Asn Asp Arg Lys
                20                  25                  30

Lys Arg

<210> SEQ ID NO 33
<211> LENGTH: 34
<212> TYPE: PRT
<213> ORGANISM: Artificial Sequence
<220> FEATURE:
<223> OTHER INFORMATION: Synthetic peptide

<400> SEQUENCE: 33

```
Tyr Pro Leu Gln Trp Ser Leu Leu Val Ala Val Val Ala Gly Ser Val
1               5                   10                  15

Val Ser Tyr Gly Val Lys Lys Arg Thr Leu Arg Lys Asn Asp Arg Lys
            20                  25                  30

Lys Arg
```

<210> SEQ ID NO 34
<211> LENGTH: 25
<212> TYPE: PRT
<213> ORGANISM: Artificial Sequence
<220> FEATURE:
<223> OTHER INFORMATION: Synthetic peptide

<400> SEQUENCE: 34

```
Gly Val Ser Thr Phe Val Thr Gly Thr Gly Ala Thr Phe Gly Leu Gln
1               5                   10                  15

Met Leu Val Arg Arg Arg Arg Arg Arg
            20                  25
```

<210> SEQ ID NO 35
<211> LENGTH: 23
<212> TYPE: PRT
<213> ORGANISM: Artificial Sequence
<220> FEATURE:
<223> OTHER INFORMATION: Synthetic peptide

<400> SEQUENCE: 35

```
Trp Lys Val Leu Leu Ala Val Val Ala Gly Ser Val Ala Ser Tyr Trp
1               5                   10                  15

Val Arg Arg Arg Arg Arg Arg
            20
```

<210> SEQ ID NO 36
<211> LENGTH: 28
<212> TYPE: PRT
<213> ORGANISM: Artificial Sequence
<220> FEATURE:
<223> OTHER INFORMATION: Synthetic peptide

<400> SEQUENCE: 36

```
Tyr Ala Phe Met Lys Gly Thr Ala Ser Phe Ile Leu Gly Thr Val Gly
1               5                   10                  15

Ile Phe Phe Gly Trp Arg Arg Gln Ala Arg Phe Lys
            20                  25
```

<210> SEQ ID NO 37
<211> LENGTH: 27
<212> TYPE: PRT
<213> ORGANISM: Artificial Sequence
<220> FEATURE:
<223> OTHER INFORMATION: Synthetic peptide

<400> SEQUENCE: 37

```
Leu Gln Trp Asn Leu Phe Val Ser Ile Val Ser Ser Val Phe Ser
1               5                   10                  15

Tyr Ser Val Trp Arg Arg Gln Ala Arg Phe Lys
            20                  25
```

<210> SEQ ID NO 38
<211> LENGTH: 29
<212> TYPE: PRT
<213> ORGANISM: Artificial Sequence
<220> FEATURE:

```
<223> OTHER INFORMATION: Synthetic peptide

<400> SEQUENCE: 38

Ala Phe Met Lys Gly Val Phe Thr Phe Val Thr Gly Thr Gly Ala Thr
1               5                   10                  15

Phe Gly Leu Leu Met Phe Ile Arg Arg Arg Arg Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Pro Val Gln Trp Ser Phe Leu Val Ser Ala Ile Ala Gly Ser Val Ala
1               5                   10                  15

Ser Tyr Arg Val Trp Arg Arg Gln Ala Arg Phe Lys
            20                  25

<210> SEQ ID NO 40
<211> LENGTH: 54
<212> TYPE: PRT
<213> ORGANISM: Artificial Sequence
<220> FEATURE:
<223> OTHER INFORMATION: Synthetic peptide

<400> SEQUENCE: 40

Arg Arg Arg Met Lys Gly Val Phe Thr Phe Val Thr Gly Thr Gly Met
1               5                   10                  15

Ala Phe Gly Leu Gln Met Phe Ile Gln Arg Lys Phe Pro Tyr Pro Leu
            20                  25                  30

Gln Trp Ser Leu Leu Val Ala Val Ala Gly Ser Val Ser Tyr
        35                  40                  45

Gly Arg Arg Arg Arg Arg
    50

<210> SEQ ID NO 41
<211> LENGTH: 27
<212> TYPE: PRT
<213> ORGANISM: Artificial Sequence
<220> FEATURE:
<223> OTHER INFORMATION: Synthetic peptide

<400> SEQUENCE: 41

Tyr Pro Leu Gln Trp Ser Leu Leu Val Ala Val Ala Gly Ser Val
1               5                   10                  15

Val Ser Tyr Gly Val Thr Arg Val Glu Ser Glu
            20                  25
```